United States Patent [19]

Baumgartner et al.

[11] 4,351,774

[45] Sep. 28, 1982

[54] PROCESS FOR THE PRODUCTION OF METHOXYANTHRAQUINONES

[75] Inventors: Peter Baumgartner, Sissach; Urs Karlen, Magden; Urs Keller, Muttenz, all of Switzerland

[73] Assignee: Ciba-Geigy AG, Basel, Switzerland

[21] Appl. No.: 132,054

[22] Filed: Mar. 20, 1980

[30] Foreign Application Priority Data

Mar. 29, 1979 [CH] Switzerland .......................... 2920/79

[51] Int. Cl.³ ............................................ C07C 49/74
[52] U.S. Cl. ....................................................... 260/383
[58] Field of Search .......................................... 260/383

[56] References Cited

U.S. PATENT DOCUMENTS 3,983,145  9/1976  White et al. ......................... 260/383

FOREIGN PATENT DOCUMENTS 2314696  10/1974  Fed. Rep. of Germany .
42-34950  8/1967  Japan .................................. 260/383
50-111058  1/1975  Japan .................................. 260/383

Primary Examiner—Thomas A. Waltz
Assistant Examiner—Raymond Covington
Attorney, Agent, or Firm—Sprung, Horn, Kramer & Woods

[57] ABSTRACT

A process for the production of methoxyanthraquinones of high purity by reaction of nitroanthraquinones with methanol and alkali, in the presence of alkali-resistant nitrous acid inhibitors.

7 Claims, No Drawings

PROCESS FOR THE PRODUCTION OF METHOXYANTHRAQUINONES

The present invention relates to an advantageous process for the production of methoxyanthraquinones of high purity by reaction of nitroanthraquinones with methanol and alkali in the presence of alkali-resistant nitrous acid inhibitors.

A process for the production of methoxyanthraquinones from nitroanthraquinones as starting materials is described in German Pat. No. 77 818. This process consists in reacting a mixture of dinitroanthraquinones, which have been obtained by dinitration of anthraquinones with an acid mixture of concentrated sulfuric acid and nitric acid, in methanol with an alkali metal hydroxide or alkaline earth metal hydroxide. However, in this process—as is mentioned in German Offenlegungsschrift No. 2 152 991—there are obtained about 30 to 40% of by-products, such as diamino-, aminomethoxy-, hydroxymethoxy-, dihydroxy- and aminoanthraquinones.

In the above cited Offenlegungsschrift, as well as in German Offenlegungsschrift No. 2 314 696, there is described a process for the production of α-methoxyanthraquinones which consists in heating α-nitroanthraquinones with potassium hydroxide or anhydrous potassium carbonate in methanol. However, these processes also do not sufficiently prevent secondary reactions and result in the production of dimethoxyanthraquinones which still contain about 10 to 20% of by-products.

German Offenlegungsschrift No. 2 607 036 describes a further process for the production of methoxyanthraquinones by reaction of nitroanthraquinones with methanol and alkali in a medium consisting of methanol, in which process gaseous molecular oxygen is introduced during the course of the reaction and the concentration of dissolved oxygen in the medium is kept at least at about 1 ppm.

While this process makes it possible to obtain products of good quality, it requires relatively complicated apparatus, as the introduction of air results in the entrainment of large amounts of methanol for which elaborate condenser units are necessary. In addition, if the reaction conditions for maintaining product quality are to be kept constant and the safety requirements are to be observed, the reaction control requires considerable investment in equipment and extensive maintenance.

In all the previously known process variants, undesired by-products appear to be nitrogen compounds of the most widely differing composition. The secondary reactions are probably caused by nitrous acid and/or its compounds. It has been found that, by carrying out the reaction in the presence of nitrous acid inhibitors which, surprisingly, are also effective in an alkaline reaction medium, virtually only pure methoxy compounds are obtained.

Alkali-resistant nitrous acid inhibitors to be used in the practice of this invention are compounds which react with nitrous acid and whose reaction rate with nitrous acid is high, but with nitric acid is low, preferably zero. Examples of such nitrous acid inhibitors are amines and amino compounds which are resistant to alkali in methanol. The purpose of their addition is to inhibit secondary reactions which are catalysed by nitrous acid. Especially suitable nitrous acid inhibitors are: primary and secondary amines, e.g. diethylamine, dipropylamine, ethylamine, tert-butylamine and, especially, sulfamic acid. The nitrous acid inhibitors are advantageously used in amounts of 80 to 120% molar equivalents, based on the nitro groups to be reacted; preferably, however, molar amounts are used.

Examples of nitroanthraquinones eligible for use as starting materials in the process of this invention are α-nitroanthraquinones, such as 1-nitroanthraquinone, 1,5-dinitroanthraquinone, 1,8-dinitroanthraquinone and a mixture thereof, and also substituted nitroanthraquinones wherein one or more hydrogen atoms are further substituted by a halogen atom, an alkyl group etc., e.g. 1-nitro-6- or 1-nitro-7-chloroanthraquinone. A mixture of 1,5- and 1,8-dinitroanthraquinones is obtained e.g. by nitrating anthraquinone with nitrosulfuric acid or with concentrated nitric acid.

Suitable alkalies for the process of the invention are hydroxides, methylates, and carbonates of alkali metals, including sodium hydroxide, potassium hydroxide, sodium methylate, potassium methylate, sodium carbonate and potassium carbonate. From the economic and technical point of view, the most advantageous alkali is potassium hydroxide. The concentration of alkali in methanol is as a rule between about 0.5 and 3.0 mole/l of methanol, preferably between about 0.8 and 2.0 mole/l of methanol.

A suitable reaction medium, which is simultaneously reagent, for the process of this invention is an excess of methanol, for example about 500 to 2000 parts by weight per 100 parts by weight of nitroanthraquinone.

The process of the invention can be carried out either under atmospheric pressure or under overpressure. In the latter case, a pressure of 5 to 40 bar is applied. The reaction temperature varies between about 50° and 130° C. The preferred temperature range at atmospheric pressure is from about 50° to 70° C., and, at overpressure, from about 70° to 110° C.

Depending on the operating requirements, the reaction conditions can be so chosen that the reaction proceeds for the corresponding length of time. When carrying out the process under pressure, the reaction time is in the region of 2 hours, while at atmospheric pressure the reaction time can be up to 30 hours. It is preferred to carry out the process at atmospheric pressure, for this method is advantageous as regards safety requirements and product quality.

The process of this invention makes it possible, in simple manner, to produce high-grade methoxyanthraquinones containing a minimum amount of impurities and having a constant degree of purity, under conditions which ensure a relatively safe and reasonably economic mode of operation.

The methoxyanthraquinones obtained are valuable intermediates for the manufacture of dyes or are themselves anthraquinones dyes which are suitable for dyeing polyester fibres. As regards the dyes obtained in this manner, there is no pollution problem caused by mercury, in contrast to anthraquinone dyes which are obtained from anthraquinone-α-sulfonic acid using a mercury catalyst, so that the invention is also of importance from the ecological point of view.

Blue polyester dyes are obtained from 1,5- and 1,8-dimethoxyanthraquinones, e.g. after nitration, ether cleavage, reduction and bromination (cf. German Pat. No. 1 029 506 and U.S. Pat. No. 2,990,413).

The process of the invention for the production of dimethoxyanthraquinones is illustrated by the following Examples, in which parts and percentages are by weight unless otherwise stated.

EXAMPLE 1

75.3 parts of potassium hydroxide, 61.3 parts of 1.5-dinitroanthraquinone (97%) and 40 parts of sulfamic acid are suspended in 1100 parts of methanol. The suspension is heated to 50°–55° C. and stirred at this temperature for 30 hours while introducing a very small amount of nitrogen over the surface of the resultant reaction solution. The reaction mixture is then cooled to room temperature and filtered. The filter cake is washed neutral with 2 liters of water, affording 53.5 parts of 1,5-dimethoxyanthraquinone of 97–98% purity.

If in this Example the sulfamic acid used as nitrous acid inhibitor is omitted, the same amount of 1,5-dimethoxyanthraquinone is obtained in a purity of only 70–80%.

EXAMPLE 2

61.3 parts of a nitroanthraquinone mixture consisting of 0.6% of 1-nitroanthraquinone, 14.7% of 1,5-dinitroanthraquinone, 3.5% of 1,6-dinitroanthraquinone, 65.0% of 1,8-dinitroanthraquinone and 16.0% of 1,7-dinitroanthraquinone, are suspended in 300 parts of methanol. A solution of 73 parts of potassium hydroxide and 40 parts of sulfamic acid in 300 parts of methanol is then added dropwise to the above suspension and the mixture is heated to reflux temperature. The reaction solution is kept for 3 hours at this temperature, then cooled to 15° C., and filtered. The filter cake is washed with warm water until the filtrate is neutral and dried, affording 51 parts of a methoxyanthraquinone mixture of the following composition: 0.5% of 1-methoxyanthraquinone, 13% of 1,5-dimethoxyanthraquinone, 2.5% of 1,6-dimethoxyanthraquinone, 14% of 1,7-dimethoxyanthraquinone, 64% of 1,8-dimethoxyanthraquinone, 1% of 1,5-dinitroanthraquinone, 1% of 1,8-dinitroanthraquinone.

EXAMPLE 3

63.25 parts of 1-nitroanthraquinone, 77 parts of potassium hydroxide and 25 parts of sulfamide are suspended in 480 parts of methanol. The suspension is stirred for 18 hours at 55° C., then cooled to 15° C., stirred for a further hour at this temperature and filtered. The filter cake is washed neutral with 3 liters of water.

Yield: 55.5 parts of 1-methoxyanthraquinone.

EXAMPLE 4

62.5 parts of 1,X-dinitroanthraquinone, 77 parts of potassium hydroxide and 40 g of sulfamic acid are suspended in 480 parts of methanol and then the temperature is raised to 50°–55° C. After 20 hours at this temperature the reaction is complete. The reaction mixture is cooled to 15° C., filtered, and the filter cake is washed neutral with 2 liters of water.

Yield: 49.5 parts of 1,X-dimethoxyanthraquinone.

EXAMPLE 5

The methanolic mother solution of Example 4 (400 parts) is bulked with 80 parts of fresh methanol and 62.5 parts of 1,X-dinitroanthraquinone, 53 g of potassium hydroxide and 40 g of sulfamic acid are suspended therein. Repetition of the same procedure as described in Example 4 yields 52 parts of 1,X-dimethoxyanthraquinone. This procedure can be repeated at least 10 times without regeneration of the mother solution or without the quality of the 1,X-dimethoxyanthraquinone being impaired.

EXAMPLE 6

In a sulfonating flask, 30 parts of a 1,8-dinitroanthraquinone, 75.3 parts of potassium hydroxide and 25 parts of dipropylamine are suspended in 550 parts of methanol. The temperature is then raised to 60° C. and the batch is stirred at this temperature for 20 hours. After all the 1,8-dinitroanthraquinone has reacted to 1,8-dimethoxyanthraquinone, the reaction mixture is cooled to 20° C. and filtered. The filter cake is washed neutral with 2 liters of water and the product is dried at 100° C. in vacuo.

Yield: 25.7 parts of 1,8-dimethoxyanthraquinone of 95% purity.

What is claimed is:

1. A process for the production of methoxyanthraquinones of high purity by reaction of nitroanthraquinones with methanol and alkali, which process comprises carrying out the reaction in the presence of an alkali-resistant nitrous acid inhibitor selected from a group consisting of primary and secondary amines, and sulfamic acid to inhibit secondary reactions which are catalyzed by nitrous acid.

2. A process according to claim 1, wherein sulfamic acid is used as nitrous acid inhibitor.

3. A process according to claim 1, wherein the reaction is carried out in the temperature range between 50° and 130° C.

4. A process according to claim 3, wherein the reaction is carried out in the temperature range between 50° and 70° C.

5. A process according to claim 1, wherein the nitrous acid inhibitor is used in amounts of 80 to 120% molar equivalents, based on the nitro groups to be reacted.

6. A process according to claim 5, wherein the nitrous acid inhibitor is used in equimolar amounts, based on the nitro groups to be reacted.

7. A process according to claim 1, wherein potassium hydroxide or sodium hydroxide is used as alkali.

* * * * *